March 27, 1956 E. S. BOERNER Plant Pat. 1,465
CHRYSANTHEMUM PLANT
Filed April 15, 1955
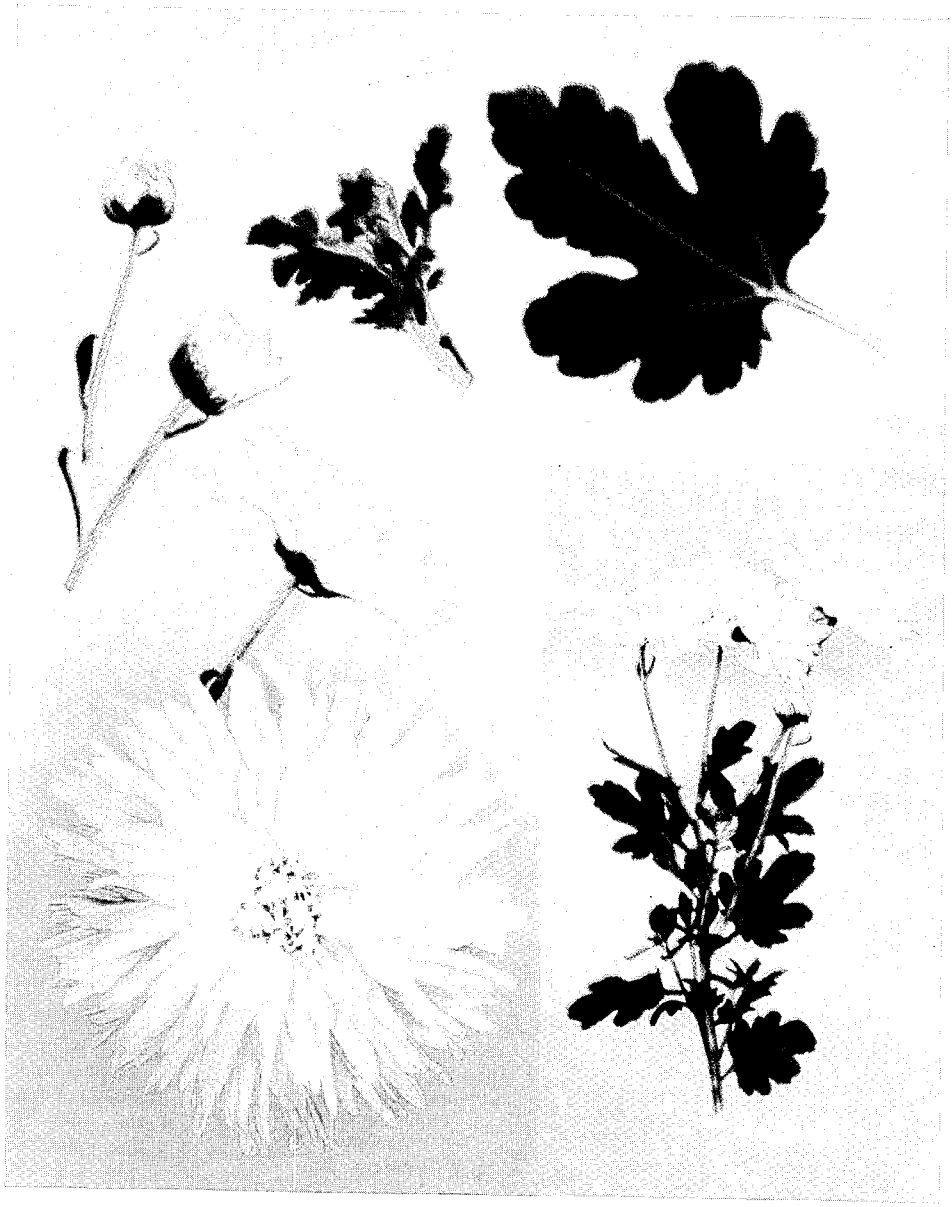
Inventor.
E. S. Boerner
By: Robb & Robb
Attorneys.

United States Patent Office

Plant Pat. 1,465
Patented Mar. 27, 1956

1,465

CHRYSANTHEMUM PLANT

Eugene S. Boerner, Newark, N. Y., assignor to Jackson & Perkins Company, Newark, N. Y., a corporation of New York Application April 15, 1955, Serial No. 501,757

1 Claim. (Cl. 47—60)

The present invention relates to a new and distinct variety of chrysanthemum plant of the decorative compound dahlia type, which was originated by me by crossing an unnamed and unpatented seedling derived from a cross of a large-flowered semi-hardy Orange seedling by "Mrs. Du Pont" with an unnamed and unpatented large-flowered Hortorum seedling.

The primary objective in making this cross was to produce a new chrysanthemum variety characterized by flowers of larger size in the yellow color range, hardier bushy plants and long flowering stems. This objective was fully achieved, as evidenced by the hardiness of the plants and flowers of my new variety which makes them excellent for garden house use, the relatively large size of the flowers, the distinctive lemon chrome color of the flowers which are lightly overcast with Pinard yellow and which in an unusual color in garden chrysanthemums, and the long, stiff stems which hold the large flowers upright at all times. These features definitely distinguish my new variety from its parents, as well as from all other varieties of its class of which I am aware.

Asexual reproduction of my new variety by top cuttings and by underground runners, as performed by me at Newark, New York, shows that the foregoing characteristics and distinctions come true to form and are established and transmitted through succeeding propagations.

The accompanying drawing shows typical specimens of the vegetative growth and the flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: An unnamed seedling derived from a cross of a large-flowered semi-hardy Orange seedling with "Mrs. Du Pont" × an unnamed large-flowered Hortorum seedling.

Classification: Decorative, compound dahlia type.

Growth: From 30 inches to 36 inches.

Cold resistance: Winter hardy in Northern New York; frost resistant flowers.

Blooming period: In the Newark, New York, climatic area, blooming starts about September 20 and the plant is very free-blooming until freezing temperatures in October or November of the average season.

FLOWER (Observations made from specimens grown in a field at Newark, New York, in the early morning in late September.)

Bud:

*Color.*—When sepals first divide—Light Greenish Yellow, Plate 5. When petals begin to unfurl—Martius Yellow, Plate 4, lightly overcast with Capucine Orange, Plate 3 on the upper tip of the petal. When half blown: inside of petals—Empire Yellow, Plate 4; outside of petals—Picric Yellow, Plate 4, lightly overcast with Orange Buff, Plate 3.

*Peduncle.*—Strength—strong; erect. Color—Light Bice Green, Plate 17.

Bloom:

*Size.*—4½ inches.

*Stem.*—Stiff; excellent keeper when cut.

*Form.*—Decorative.

*Petalage.*—Double.

*Color.*—Center of flower—Lemon Chrome, Plate 4, lightly overcast with Light Cadmium, Plate 4. Outer petals—Barium Yellow, Plate 16, lightly overcast with Martius Yellow, Plate 4. Base of petals—Light Lumiere Green, Plate 17. Inside of petals—Lemon Chrome, Plate 4, lightly overcast with Pinard Yellow, Plate 4. Reverse of petals—Picric Yellow, Plate 4.

*Petals.*—Texture—thick. Form—full; double.

*Fragrance.*—Characteristic chrysanthemum.

PLANT

Form: Bushy; compact; produces large mound of blooms.

Growth: Free; stiff stems; withstands storms.

Foliage:

*Size.*—Medium.

*Quantity.*—Normal.

*Color.*—Upper side—Yew Green, Plate 31. Reverse side—Oil Green, Plate 5.

*Texture.*—Leathery.

I claim:

A new and distinct variety of chrysanthemum plant of the hardy outdoor decorative compound dahlia type, substantially as herein shown and described, characterized particularly as to novelty by the large size of its flowers and the stiffness of its long stems which hold the large flowers upright at all times, and the distinctive and unusual Lemon Chrome, lightly overcast with Pinard Yellow general color tonality of the flowers.

No references cited.